(12) United States Patent
Schwab

(10) Patent No.: US 8,062,365 B2
(45) Date of Patent: Nov. 22, 2011

(54) BONE SUPPORTING DEVICES WITH BIO-ABSORBABLE END MEMBERS

(75) Inventor: Frank J. Schwab, New York, NY (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1868 days.

(21) Appl. No.: 10/633,901

(22) Filed: Aug. 4, 2003

(65) Prior Publication Data

US 2005/0033425 A1 Feb. 10, 2005

(51) Int. Cl.
*A61F 2/44* (2006.01)
(52) U.S. Cl. ...................................... 623/17.11
(58) Field of Classification Search ..... 623/17.11–17.16
See application file for complete search history.

(56) References Cited

U.S. PATENT DOCUMENTS

| | | | | |
|---|---|---|---|---|
| 2,334,817 A * | 11/1943 | Gerahty | | 229/5.7 |
| 3,355,061 A * | 11/1967 | Ritter | | 220/792 |
| 3,913,774 A * | 10/1975 | Vajtay | | 220/4.01 |
| 4,713,076 A * | 12/1987 | Draenert | | 623/23.6 |
| 4,826,008 A * | 5/1989 | Cloosterman | | 206/413 |
| 4,961,740 A * | 10/1990 | Ray et al. | | 606/61 |
| 4,982,870 A * | 1/1991 | Van Loon | | 220/586 |
| 5,816,437 A * | 10/1998 | Lin | | 220/611 |
| 5,897,556 A * | 4/1999 | Drewry et al. | | 606/61 |
| 6,086,613 A * | 7/2000 | Camino et al. | | 623/17.16 |
| 6,139,585 A | 10/2000 | Li | | |
| 6,261,322 B1 | 7/2001 | Despres, III et al. | | |
| 6,371,985 B1 | 4/2002 | Goldberg | | |
| 6,447,543 B1 * | 9/2002 | Studer et al. | | 623/17.11 |
| 6,585,770 B1 * | 7/2003 | White et al. | | 623/17.11 |
| D493,533 S * | 7/2004 | Blain | | D24/155 |
| 2001/0014826 A1 * | 8/2001 | Biedermann et al. | | 623/17.11 |
| 2001/0056302 A1 * | 12/2001 | Boyer et al. | | 623/17.15 |
| 2002/0016635 A1 | 2/2002 | Despres, III et al. | | |
| 2002/0082701 A1 | 6/2002 | Zdeblick et al. | | |
| 2002/0138142 A1 * | 9/2002 | Castro et al. | | 623/17.11 |
| 2002/0156529 A1 | 10/2002 | Li et al. | | |
| 2002/0173850 A1 | 11/2002 | Brodke et al. | | |
| 2003/0065393 A1 | 4/2003 | Moumene et al. | | |
| 2003/0181980 A1 * | 9/2003 | Berry et al. | | 623/17.11 |

FOREIGN PATENT DOCUMENTS

WO WO 99/32055 7/1999

(Continued)

OTHER PUBLICATIONS

46th Annual Meeting, Orthopaedic Research Society, Mar. 12-15, 2000, Orlando Florida; "The Mechanics of Absorbable Spinal Cages Perforating the Endplates: An In Vitro Study", Smith, T.; Van Dijk, M.; Arnoe, M.; Wuisman, P.

(Continued)

*Primary Examiner* — Eduardo C Robert
*Assistant Examiner* — Mary Hoffman

(57) ABSTRACT

A device for supporting adjacent bony portions includes a body having a first end and an opposite second end. The body is positionable in a space between the adjacent bony portions with the first and second ends oriented toward respective ones of the adjacent bony portions. At least one of the first and second ends includes bone engaging surfaces. An end member substantially covers the bone engaging surfaces with a bio-absorbable material on at least one end of the body. The end member providing a smooth surface profile to facilitate insertion of the body in the space between the adjacent bony portions.

20 Claims, 3 Drawing Sheets

FOREIGN PATENT DOCUMENTS

WO    WO 02/34168 A1    5/2002

OTHER PUBLICATIONS

Orthopedics, Oct. 2002 Supplement; "Bioresorbable Polymer Implants in the Unilateral Transforaminal Lumbar Interbody Fusion Procedure"; Thomas G. Lowe, MD, Jeffrey D. Coe, MD, pp. 1-9.

Orthopedics, Oct. 2002 Supplement; "Spinal Applications of Bioabsorbable Implants"; Alexander R. Vaccaro, MD, guest editor; Luke Madigan, MD, pp. 1-11.

Orthopedics, Oct. 2002 Supplement; "Applications of a Resorbable Interbody Spacer via Posterior Lumbar Interbody Fusion Technique"; Joseph T. Alexander, MD, Charles L. Branch, Jr., MD, Brian R. Subach, MD, Regis W. Haid, Jr., pp. 1-9.

* cited by examiner

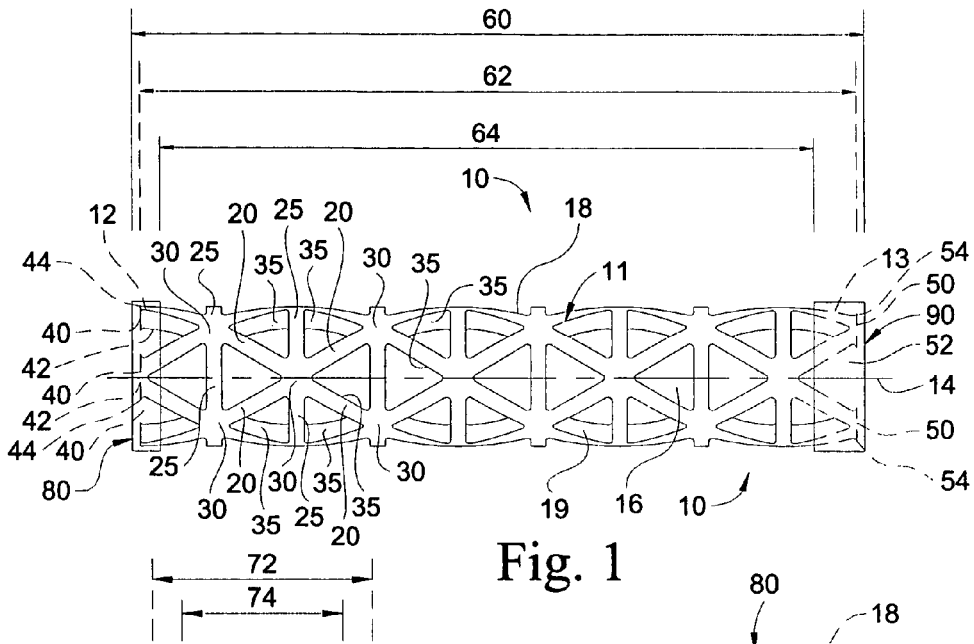
Fig. 1
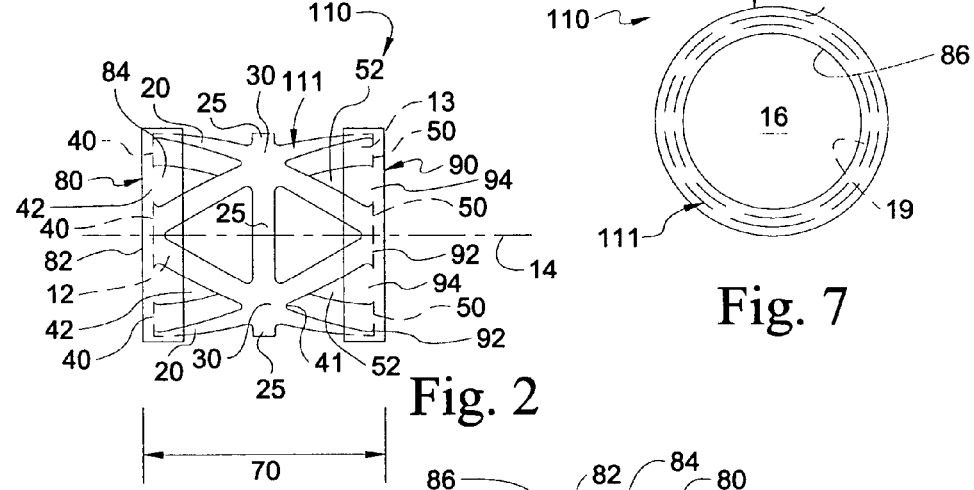
Fig. 2
Fig. 7
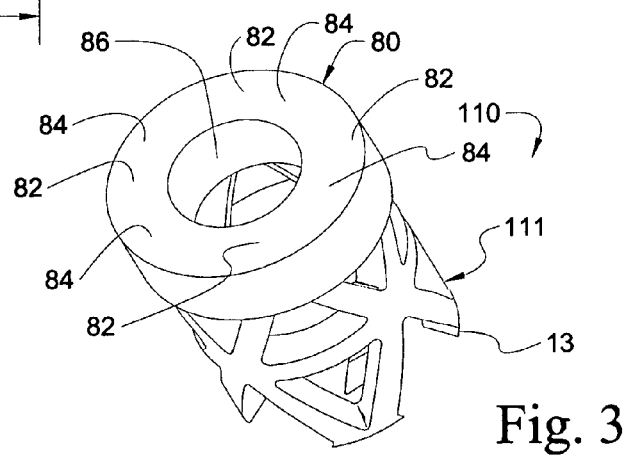
Fig. 3

BONE SUPPORTING DEVICES WITH BIO-ABSORBABLE END MEMBERS

BACKGROUND

The repair and reconstruction of bony structures is sometimes accomplished by directly fixing adjacent bony portions to each other, such as by a plate. In other instances, bone growth inducing material can be introduced between the adjacent bony portions, which over time results in a solid bony connection. In some instances, the adjacent bony portions are supported by an implant positioned therebetween as the bone heals or the bone grows between the adjacent portions. In order to secure the implant in the space between the adjacent bony portions, the bone engaging ends of the implants can be provided with bone engaging surfaces. The bone engaging surfaces, however, can cause undesired cutting or tearing of tissue as the implant is positioned in the desired location between the bony portions. Positioning of the implant can be difficult if the implant engages tissue as it is moved into position.

SUMMARY

The invention relates to devices positionable between adjacent bony portions having at least one end member comprised of bio-absorbable material.

According to one aspect, a device for supporting adjacent bony portions includes a body having a first end and an opposite second end. The body is positionable in a space between the adjacent bony portions with the first and second ends oriented toward respective ones of the adjacent bony portions. At least one of said first and second ends includes bone engaging surfaces thereon. The device further includes an end member at the at least one of the first and second ends. The end member substantially covers the bone engaging surfaces with a bio-absorbable material to provide a smooth surface profile to facilitate insertion of the body in the space between the adjacent bony portions.

According to another aspect, a device for supporting adjacent bony portions includes a body having a first end and an opposite second end. The body is positionable in a space between the adjacent bony portions with the first and second ends oriented toward respective ones of the adjacent bony portions. The body has a first height between the first and second ends. The device further includes a bio-absorbable member about the body and extending from a first end to a second end adjacent respective ones of the first and second ends of the body. The bio-absorbable member has a second height between said first and second ends thereof that is greater than the first height.

According to a further aspect, a method for supporting adjacent bony portions comprises: providing a device including a body having first and second ends and at least one bio-absorbable end member over one of the first and second ends; positioning the device between the adjacent bony portions with the end member in contact with at least one of the adjacent bony portions; and resorbing the end member so the one end contacts the adjacent bony portion.

Other objects, features, aspects, embodiments and particular advantages of the present invention can be discerned from the following written description and accompanying figures.

BRIEF DESCRIPTION OF THE FIGURES

FIG. 1 is an elevation view of one embodiment device with end members.

FIG. 2 is an elevation view of another embodiment device with end members.

FIG. 3 is a perspective view of the device of FIG. 2 with one end member.

FIG. 7 is a plan view of the device of FIG. 2.

DESCRIPTION OF THE ILLUSTRATED EMBODIMENTS

Figure 4:
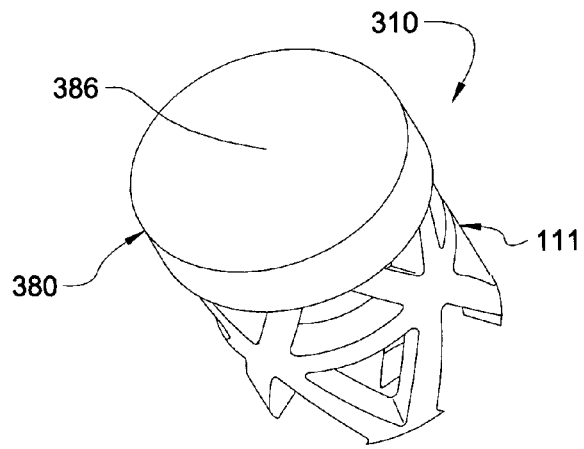
FIG. 4 is a perspective view of the device of FIG. 2 with another embodiment end member.

For the purpose of promoting an understanding of the principles of the invention, reference will now be made to embodiments thereof and specific language will be used to describe the same. It will nevertheless be understood that no limitation of the scope of the invention is thereby intended. Any such alterations and further modifications in the invention, and any such further applications of the principles of the invention as described herein are contemplated as would normally occur to one skilled in the art to which the invention relates.

The invention contemplates a device positionable in a space between adjacent bony portions that supports the bony portions. The device includes opposite ends having bone engaging surfaces. At least one of the opposite ends includes an end member comprised of bio-absorbable material that substantially covers the bone engaging surfaces to facilitate placement of the device between adjacent bony portions.

In FIG. 1, a device 10 includes a body 11 extending along a longitudinal axis 14. Body 11 includes a first end 12 and an opposite second end 13. Body 11 includes an outer surface 18 and an inner surface 19. Inner surface 19 defines a chamber 16 extending between and opening at ends 12, 13. Device 10 includes a first end member 80 adjacent first end 12, and a second end member 90 adjacent second end 13.

First end 12 includes a number of bone engaging surfaces 40 formed thereabout. Second end 13 includes a number of bone engaging surfaces 50 formed thereabout. Bone engaging surfaces 40, 50 engage the bone and/or tissue of the adjacent bony portion to facilitate in maintaining the position of device 10 in the space between the adjacent bony portions. The height of body 11 between ends 12, 13 can be selected to correspond to the desired spacing between the adjacent bony portions. Accordingly, as body 11 is inserted in the space between bony portions, bone engaging surfaces 40, 50 can catch, snag or otherwise contact the bony portions before body 11 is moved to its desired implantation location. End members 80, 90 provide a smooth end surface adjacent each of the ends 12, 13 to facilitate positioning of device 10 in the space between the bony portions. End members 80, 90 provide a barrier between the bone engaging surfaces 40, 50 and the bone and tissue along which device is moved as it is positioned in the space between adjacent bony portions.

In one specific embodiment, body 11 is formed by a first group of bars 20 and a second group of bars 25. The first group of angled bars 20 are oriented at non-perpendicular or nonparallel angles relative to longitudinal axis 14 of body 11. The second group of perpendicular bars 25 are aligned with their axes substantially perpendicular to longitudinal axis 14 of the tubular body. The outer surfaces of the bars 20, 25 define the cylindrical outer surface 18 and the inner surfaces of bars 20, 25 define the inner surface 19. The groups of bars are connected to each other at a plurality of interior joints 30. Two perpendicular bars 25 and four angled bars 20 converge at a single joint 30. With the illustrated arrangement of angled bars 20 and perpendicular bars 25, body 11 defines a plurality of triangular openings 35. Each triangular opening is defined by two angled bars 20 and one perpendicular bar 25.

Other embodiments contemplate other forms for body 11, including mesh structures with circular, diamond, square, oval, or other shaped wall openings. Body 11 can be provided in the form of a ring having a solid wall, or a wall with one or more openings extending between interior and exterior surfaces of the ring. The ring can have upper and lower end surfaces forming a circular shape, oval, D-shape, U-shape, square, rectangular, polygonal, arcuate, or any other suitable shape. It is further contemplated that body 11 can be provided as a block of material that is solid, porous, or include one or more perforations, openings, channels, and/or cavities extending therethrough between upper and lower surfaces thereof.

In the illustrated embodiment, body 11 includes bone engaging surface 40, 50 formed by the intersection or union of a pair of angled bars 20. Engaging surfaces 40 are spaced from one another by recesses 42 spaced about first end 12. Similarly, engaging surfaces 50 are spaced from one another by recesses 52 spaced about second end 13. Recesses 42 each include a triangular shape having a base portion that opens toward first end 12 such that a discontinuity is formed between adjacent ones of the engaging surfaces 40. Similarly, recesses 52 each include a triangular shape having a base portion that opens toward second end 13 such that a discontinuity is formed between adjacent ones of the engaging surfaces 50. The discontinuities between engaging surfaces 40 and engaging surfaces 50 facilitate the engagement of engaging surfaces 40, 50 with the bone or tissue supported thereby.

In the illustrated embodiment, engaging surfaces 40, 50 each include a flat plateau-like upper surface and edges about each of the flat surfaces that can penetrate into the adjacent bony portion. Other forms for engaging surfaces 40, 50 are also contemplated. For example, engaging surface 40, 50 can be in the form of teeth, spikes, ridges, knurlings, peaks, barbs, wedges, or other structure having surface discontinuities that facilitate engagement of the ends of the device with the adjacent bony portion. It is further contemplated that ends 12, 13 can be parallel to one another, angled relative to one another, include curvature to conform to the endplate anatomy, or any other suitable shape or orientation relative to one another.

End member 80 is located adjacent first end 12, and is configured to substantially cover engaging surfaces 40. Similarly, end member 90 is located adjacent second end 13, and is configured to substantially cover engaging surfaces 50. Accordingly, as device 10 is inserted in the space between adjacent bony portions, end members 80, 90 prevent engaging surfaces 40, 50, respectively, from contacting the adjacent bony portions as device 10 is moved into position. Accordingly movement to the desired position between the adjacent bony portions is not inhibited by engaging surfaces 40, 50 contacting, biting into, snagging or otherwise resisting movement of device 10 by engagement with the adjacent bony tissue or soft tissue portions.

Body 11 includes a length 62 between the opposite engaging surfaces 40, 50. With end members 80, 90 device 10 has a length 60 between the outwardly facing end surfaces of end members 80, 90. Accordingly, end members 80, 90 can extend from the adjacent engaging surface 40, 50 to increase the overall length of device 10. End members 80, 90 extend along body 11 such that the adjacent ends of end members 80, 90 are separated by a distance 64, which can be less than lengths 60 and 62.

In FIG. 2, another embodiment device 110 includes a body 111 that is substantially identical to body 11 discussed above. Accordingly like elements are designated with like reference numerals. Body 111, however, has a length 72 between engaging surface 40, 50 at the ends of body 111. Device 110 includes a length 70 between the outwardly facing ends of end members 80, 90, and a length 74 between the inner ends of end members 80, 90 that can be less than length 70. Length 72 of body 111 is relatively shorter than length 62 of body 11. Length 72 of body 111 is adapted for positioning in, for example, a disc space between adjacent vertebrae. Length 62 of body 11 is adapted for positioning in, for example, a space between vertebral positioned on each side of one or more removed vertebrae of a spinal column segment.

As shown in FIG. 3 with respect to device 110 and end member 80, end member 80 can form a continuous ring about the end 12. For example, end member 80 extends along inner surface 19 and outer surface 18 of body 111. An opening 86 is provided through end member 80 so chamber 16 can be in communication with the adjacent bony portion supported by the ends of device 110. Other embodiments contemplate end members that do not extend along one or both of the inner surface 19 and outer surface 18, but rather cover only engaging surfaces 40 to maximize the size of opening 86. It is further contemplated that the device can be provided with an end member at only one end, such as shown in FIG. 3. Still other embodiments, such as shown in FIG. 4, contemplate a device 310 in which end member 380 includes a substantially solid end surface 386. End member 380 can assist in maintaining bone growth material and other material in chamber 16 until end member 380 has sufficiently resorbed or degraded.

Referring again to FIG. 2, end member 80 includes first portions 82 positioned over each of the engaging surfaces 40, and second portions 84 extending between adjacent ones of the first portions 82 to form a continuous ring about first end 12. Second portions 84 span recesses or discontinuities 42 formed between adjacent ones of the engaging surfaces 40 to provide a smooth contact surface to facilitate insertion of device 110. End member 90 can be similarly configured with first portions 92 and second portions 94.

End members 80, 90 are made from resorbable or bioabsorbable material so that over time end members 80, 90 will resorb or otherwise degrade, placing engaging surfaces 40, 50 into contact with and in direct engagement with the adjacent surfaces of the adjacent bony portions. Examples of resorbable materials including polylactide, polyglycolide, tyrosine-derived polycarbonate, polyanhydride, polyorthoester, polyphosphazene, calcium phosphate, hydroxyapatite, bioactive glass, collagen, albumin, fibrinogen and combinations thereof.

Body 11 can be made from a metal, polymer, or other suitable biocompatible material that provides long-term stability and support to the adjacent bony segments. The body of the devices can be made from any biocompatible material, including synthetic or natural autograft, allograft or xenograft tissues, and can be non-resorbable in nature. Examples of tissue materials include hard tissues, connective tissues, demineralized bone matrix and combinations thereof. Examples of non-resorbable materials include non-reinforced polymers, carbon-reinforced polymer composites, PEEK and PEEK composites, shape-memory alloys, titanium, titanium alloys, cobalt chrome alloys, stainless steel, ceramics and combinations thereof and others as well. Still other embodiments contemplate that body 11, 111 is made from a resorbable material that resorbs over time while providing stability and support until fusion or healing of the adjacent bony segments has occurred. In such embodiments, end members 80, 90 rapidly degrade while the body of the implant degrades slowly over time to support the adjacent bony portions to obtain bony fusion.

As end members 80, 90 resorb post-implantation, the adjacent bony portions can be allowed to settle toward ends 12, 13 of body 11 for engagement therewith, providing post-operative stability and a secured implantation location for device 10. Various degradation parameters for end members 80, 90 are contemplated. For example, end members 80, 90 can be adapted to resorb over a relatively short time period so that relative immediate post-implantation engagement of engaging surfaces 40, 50 with the adjacent bony portion can be provided to ensure long-term stability. In one example, degradation occurs in a matter of hours, such as 4 to 48 hours, to provide engagement relatively soon after implantation. In another example, degradation occurs over several days, such as three to 10 days. In a further example, degradation occurs over several weeks, such as two to six weeks.

Supplemental stabilization with, for example, rods, plates, staples or other devices secured to the adjacent bony portions can maintain stabilization during bio-absorption of the end members and fusion of the adjacent bony portions. The supplemental stabilization devices can be dynamically attached to the adjacent bony portions to allow settling of the adjacent bony portions as the end members degrade. In any event, it is contemplated that end members 80, 90 degrade in sufficient time so that engaging surfaces 40, 50 eventually engage the adjacent bony portions to provide stability during fusion. Post-implantation settling of the adjacent bony portions as end members 80, 90 degrade can facilitate bony fusion between the adjacent bony portions by maintaining contact between the bone growth material in chamber 16 and the adjacent bony portions. In addition, maintenance of compression on the implanted device and the graft or bone material with the adjacent bony portions can enhance fusion rates.

Figure 5:
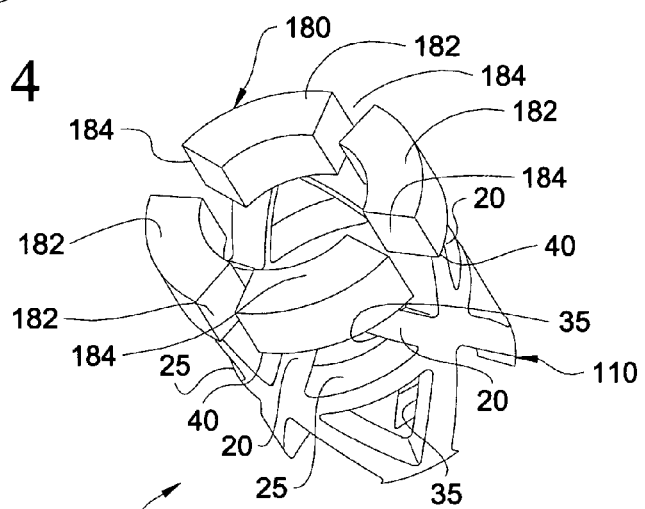
FIG. 5 is a perspective view of the device of FIG. 2 with another embodiment end member.

Referring now to FIG. 5, there is shown another embodiment of the end members with device 110. End member 180 includes a number of first portions 182 that cover respective ones of the bone engaging surfaces 40. A number of spaces 184 are provided between adjacent ones of the end member portions 182 that correspond to the locations of the respective recesses 42 between adjacent ones of the bone engaging surfaces 40. In this embodiment, the rigid bone engaging structures are covered by a bio-absorbable material that prevents the bone engaging surface from engaging bone or other tissue adjacent the space as device 110 is positioned in the space.

Figure 6:
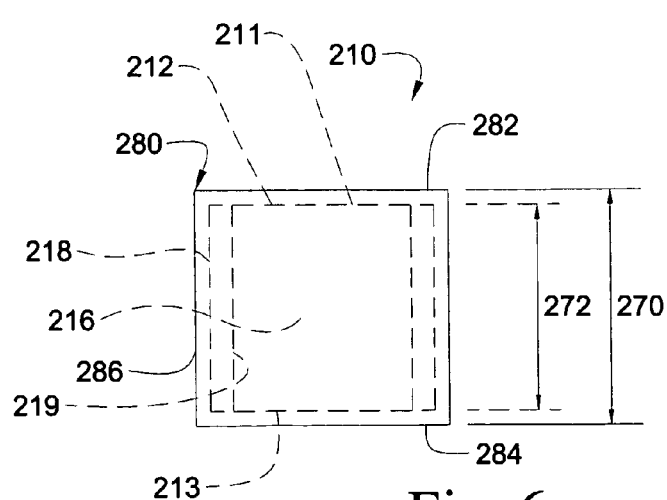
FIG. 6 is an elevation view of another embodiment device.

Another embodiment device 210 is shown in FIG. 6. Device 210 includes a body 211 substantially encapsulated by resorbable member 280. Body 211 can be configured such as discussed above with respect to bodies 11, 111, and includes a first end 212, an opposite second end 213. Body 211 can include a chamber 216 between ends 212, 213. Body 212 can also be a solid body, a body with a plurality of holes, or a body with upper and lower end walls that are solid or include one or more holes. Ends 212, 213 can be provided with bone engaging surfaces.

Resorbable member 280 includes a first end member 282 that substantially covers the bone engaging surfaces at first end 212, and a second end member 284 that substantially covers the bone engaging surfaces at second end 213. Resorbable member 280 further includes a body portion 286 that extends between and connects first and second end members 282, 284. Body portion 286 can extend along the inner and outer surfaces 219, 218 of body 211 between end members 282, 284. Alternatively, body portion 286 can extend along one of the inner and outer surfaces of body 211. In a further embodiment, resorbable member 280 substantially covers each of the ends 212, 213 and encloses chamber 216. Bone growth material or other substance, device, or graft can be pre-packed or pre-positioned in chamber 216 and encapsulated by resorbable member 280 and/or enclosed by end members 282, 284.

Body 211 includes a height 272 between first end 212 and second end 213 sized to fit the space between the adjacent bony portions. Resorbable member 280 includes a height 270 between its opposite ends greater than height 272. As resorbable member 280 resorbs over time, engaging surfaces at ends 212, 213 contact the adjacent bony portions to provide long term support and stability thereof. Further, the post-implantation settling of the adjacent bony portions can facilitate bony fusion between the adjacent bony portions by maintaining contact with bone growth material in chamber 216 and maintain poster-operative compression of the adjacent bony portions with the fusion device, graft, and/or other bone growth material between the adjacent bony portions.

Figure 8:
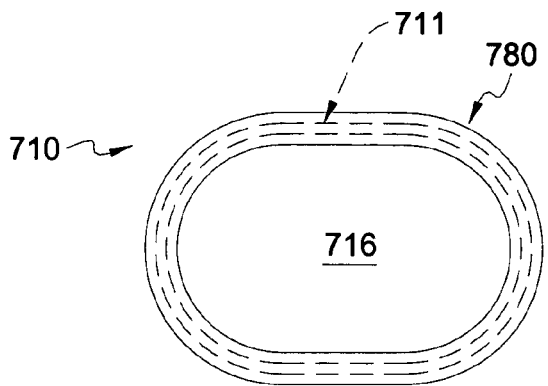
FIG. 8 is a plan view of another embodiment device with at least one end member.
Figure 9:
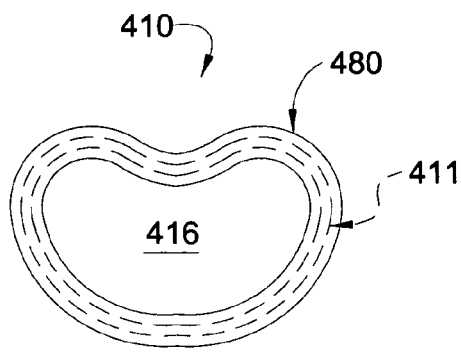
FIG. 9 is a plan view of another embodiment device with at least one end member.
Figure 10:
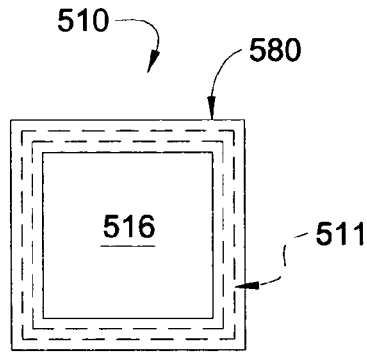
FIG. 10 is a plan view of another embodiment device with at least one end member.
Figure 11:
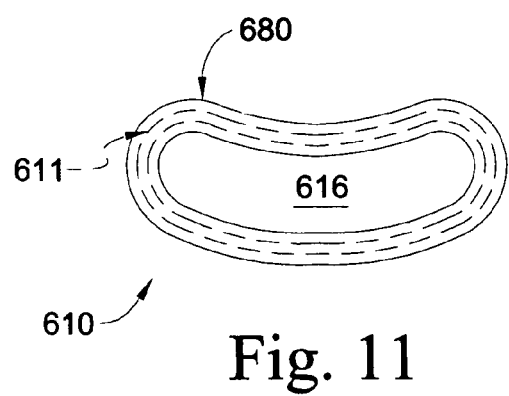
FIG. 11 is a plan view of another embodiment device with at least one end member.

In the embodiments of FIGS. 1 and 2, devices 10, 110 include bodies 11, 111 with a circular shape at each end 12, 13, such as shown in FIG. 7. End members 80, 90 have a shape that corresponds to the shape of bodies 11, 111. Other shapes are also contemplated. For example, in FIG. 8, device 310 includes a body 311 having an oval or racetrack shape defining a chamber 716. End member 780 includes an oval or racetrack shape extending thereabout either continuously or discontinuously as discussed above. In FIG. 9, device 410 includes a body 411 having a kidney shape defining a chamber 416. End member 480 includes a kidney extending thereabout either continuously or discontinuously as discussed above. In FIG. 10, device 510 includes a body 511 having a square or rectangular shape defining a chamber 516. End member 580 includes a square or rectangular shape extending thereabout either continuously or discontinuously as discussed above. In FIG. 11, device 610 includes a body 611 having a boomerang or banana shape defining a chamber 616. End member 680 includes a boomerang or banana shape extending thereabout either continuously or discontinuously as discussed above. Other shapes are also contemplated, including U-shapes, D-shapes, polygonal shapes, and shapes that combine linear and arcuate segments, for example.

In use, the devices with end members can be positioned in the space between adjacent bony portions so that the end members are in contact with surfaces of the adjacent bony portions. As the end members resorb or degrade over time, the engaging surfaces at the ends of the body of the device engage the adjacent bone portions to further stabilize the position of the device in the space between the adjacent bony portions. The devices can be used to hold the adjacent bony portions in immediate contact. Alternatively, the devices can hold the bony portions apart so that a gap is formed between the portions. In these instances, the hollow chambers of each of the devices can be filled with bone growth inducing or osteogenetic material.

In another use of the devices, the devices can be directly and entirely situated in the gap between adjacent bony portions that include adjacent vertebrae of the spinal column. In this application, the bone engaging surfaces at the opposite ends of the body of the device can be positioned to directly contact the bone of the adjacent vertebral endplates upon sufficient degradation of the end members. It is contemplated that the engaging surfaces can be positioned to at least contact the hard cortical bone at the outer perimeter of the vertebral endplates. When used in this manner, the hollow chamber of the devices can be filled with a graft and/or an osteogenetic or bone growth material.

Any suitable osteogenetic material or composition is contemplated for placement within the chambers of the devices discussed herein. Such osteogenic material includes, for example, autograft, allograft, xenograft, demineralized bone, synthetic and natural bone graft substitutes, such as bioceramics and polymers, and osteoinductive factors. Where bony material is placed within the chamber, the material can be pre-packed into the hollow chambers before the device is implanted, or can be pushed through the plurality of wall openings after the device is in position in the spinal column. A separate carrier to hold the materials within the chamber of the device can also be used. These carriers can include collagen-based carriers, bioceramic materials, such as BIO-GLASS®, hydroxyapatite and calcium phosphate compositions. The carrier material can be provided in the form of a sponge, a block, folded sheet, putty, paste, graft material or other suitable form. Moreover, the osteogenetic compositions contained within the device can comprise an effective amount of a bone morphogenetic protein, transforming growth factor 1, insulin-like growth factor 1, platelet-derived growth factor, fibroblast growth factor, LIM mineralization protein (LMP), and combinations thereof or other therapeutic or infection resistant agent, held within a suitable carrier material.

While the invention has been illustrated and described in detail in the drawings and foregoing description, the same is to be considered as illustrative and not restrictive in character. All changes and modifications that come within the spirit of the invention are desired to be protected.

What is claimed is:

1. A device for supporting adjacent bony portions, comprising:
    a body having a first end and an opposite second end, said body positionable in a space between the adjacent bony portions with said first and second ends oriented toward respective ones of the adjacent bony portions, wherein said body includes an outer surface and an opposite inner surface adjacent at least one of said first and second ends and said at least one of said first and second ends including bone engaging surfaces thereon, said bone engaging surfaces being separated from one another by recesses located therebetween that extend between said inner and outer surfaces of said body; and
    an end member around said at least one of said first and second ends, said end member substantially covering said bone engaging surfaces with a smooth surface profile between said bone engaging surfaces to facilitate insertion of said body in the space between the adjacent bony portions wherein said end member extends from said bone engaging surfaces at said at least one of said first and second ends and along said inner and outer surfaces of said body toward the other of said first and second ends, wherein said end member is configured with respect to said body to prevent said bone engaging surfaces from engaging the respective adjacent bony portion during movement of said body into the space between the adjacent bony portions, and further wherein said end member is composed of material that degrades over time to permit the adjacent bony portions to settle toward said at least one of said first and second ends to position said bone engaging surfaces thereof in engagement with the respective adjacent bony portion.

2. The device according to claim 1, wherein said bone engaging surfaces on said at least one end engage the adjacent bony portion when said end member is substantially degraded.

3. The device according to claim 1, wherein said body includes a hollow chamber extending between said first and second ends.

4. The device of claim 3, further comprising bone growth material in said chamber.

5. The device of claim 3, wherein said chamber is defined by said inner surface of said body, said end member extending at least partially into said chamber.

6. The device of claim 1, wherein said bone engaging surfaces include discontinuities therebetween, said end member occupying said discontinuities to provide said smooth surface profile.

7. The device of claim 1, wherein said body includes a wall, said wall including a plurality of openings therethrough in communication with a hollow chamber in said body, said hollow chamber extending between said first end and said second end.

8. The device of claim 7, wherein said end member extends about said chamber.

9. The device of claim 7, wherein said end member is a continuous ring extending about said at least one of said first end and said second end, said end member including a central opening in communication with said chamber.

10. The device according to claim 7, wherein said wall is comprised of a mesh structure.

11. The device of claim 7, wherein said end member provides an end surface that encloses said chamber.

12. The device of claim 1, wherein the other of said first and second ends includes bone engaging surfaces and further comprising a second end member around said other end, said second end member substantially covering said bone engaging surfaces on said other end with a bio-absorbable material and providing a smooth surface profile to facilitate insertion of said body in the space between the adjacent bony portions.

13. The device according to claim 12, wherein said bone engaging surfaces on each of said first and second ends engage the adjacent bony portion when said end members are substantially degraded.

14. The device according to claim 12, wherein said body includes a hollow chamber extending between said first and second ends, each of said end members extending about said chamber.

15. The device of claim 12, wherein said bone engaging surfaces at each of said first and second ends include discontinuities therebetween, each of said end members occupying said discontinuities to provide said smooth surface profile.

16. The device of claim 12, wherein each of said end members forms a continuous ring about said end of said body.

17. The device of claim 12, wherein said body includes a first height between said first and second ends and a second height between outer ends of said end members, said second height being greater than said first height.

18. The device of claim 1, wherein said body includes a cross-sectional shape between said first and second ends selected from the group consisting of: a circular shape, an oval shape, a kidney shape, and a boomerang shape.

19. The device of claim 1, wherein said end member extends along substantially the entire length of said body between said first and second ends.

20. The device of claim 1, wherein said end member includes a number of end member portions substantially covering respective ones of said bone engaging surfaces, said end member portions being spaced from one another about said at least one of said first and second ends.

* * * * *